US012569347B2

(12) United States Patent
Wogoman et al.

(10) Patent No.: US 12,569,347 B2
(45) Date of Patent: Mar. 10, 2026

(54) METAL-REINFORCED POLYMER FEMORAL COMPONENT OF AN ORTHOPAEDIC KNEE PROSTHESIS AND ASSOCIATED METHOD OF MAKING THE SAME

(71) Applicant: DePuy Ireland Unlimited Company, Ringaskiddy (IE)

(72) Inventors: Thomas E. Wogoman, Warsaw, IN (US); Travis D. Bennett, Huntington, IN (US); Dustin N. Albert, Warsaw, IN (US); Rajendra K. Kasinath, Warsaw, IN (US); Bryan J. Smith, Warsaw, IN (US); David A.B. Smith, Warsaw, IN (US); Daniel J. Denney, Warsaw, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 533 days.

(21) Appl. No.: 18/128,000

(22) Filed: Mar. 29, 2023

(65) Prior Publication Data

US 2024/0325160 A1    Oct. 3, 2024

(51) Int. Cl.
| | |
|---|---|
| *A61F 2/38* | (2006.01) |
| *A61F 2/30* | (2006.01) |
| *B33Y 80/00* | (2015.01) |

(52) U.S. Cl.
CPC ........ *A61F 2/3859* (2013.01); *A61F 2/30771* (2013.01); *A61F 2/3094* (2013.01); *A61F 2/389* (2013.01); *B33Y 80/00* (2014.12); *A61F 2002/30433* (2013.01); *A61F 2002/30828* (2013.01); *A61F 2002/3092* (2013.01)

(58) Field of Classification Search
CPC ................ A61F 2/3859; A61F 2/30767; A61F 2002/30973; A61F 2002/30957; A61F 2002/30067; A61F 2002/30985
See application file for complete search history.

(56) References Cited

U.S. PATENT DOCUMENTS

| | | | |
|---|---|---|---|
| 4,479,271 | A | 10/1984 | Bolesky et al. |
| 4,997,445 | A | 3/1991 | Hodorek |
| 5,019,104 | A | 5/1991 | Whiteside et al. |
| 5,702,465 | A | 12/1997 | Burkinshaw |
| 6,682,567 | B1 | 1/2004 | Schroeder |
| 6,966,928 | B2 | 11/2005 | Fell et al. |
| 7,578,851 | B2 | 8/2009 | Dong et al. |
| 7,819,925 | B2 | 10/2010 | King et al. |
| 8,157,868 | B2 | 4/2012 | Walker et al. |

(Continued)

FOREIGN PATENT DOCUMENTS

| | | |
|---|---|---|
| AU | 2010237755 A1 | 5/2011 |
| EP | 1992309 B1 | 4/2011 |

(Continued)

OTHER PUBLICATIONS

PCT International Search Report mailed Jun. 10, 2024 in application No. PCT/EP2024/058074, 13 pages.

*Primary Examiner* — Javier G Blanco
(74) *Attorney, Agent, or Firm* — Barnes & Thornburg LLP

(57) ABSTRACT

An orthopaedic knee prosthesis includes a femoral component having a metal base with a polymer articular layer molded thereto. A method for making a metal-reinforced femoral component of an orthopaedic knee prosthesis is also disclosed.

20 Claims, 5 Drawing Sheets

(56) References Cited

U.S. PATENT DOCUMENTS

| | | | |
|---|---|---|---|
| 8,333,805 | B2 | 12/2012 | Williams, III et al. |
| 8,727,203 | B2 | 5/2014 | Wang et al. |
| 8,771,364 | B2 | 7/2014 | May et al. |
| 8,864,826 | B2 | 10/2014 | Pressacco |
| 9,193,033 | B2 | 11/2015 | Zhang et al. |
| 9,757,242 | B2 | 9/2017 | Dong et al. |
| 9,801,974 | B2 | 10/2017 | Landon |
| 9,848,986 | B2 | 12/2017 | Jones et al. |
| 9,907,660 | B2 | 3/2018 | Wang et al. |
| 9,956,048 | B2 | 5/2018 | Bojarski et al. |
| 11,364,123 | B2 | 6/2022 | Tong et al. |
| 2004/0034432 | A1 | 2/2004 | Hughes et al. |
| 2007/0255412 | A1 | 11/2007 | Hajaj et al. |
| 2008/0215157 | A1 | 9/2008 | Earl et al. |
| 2009/0084491 | A1 | 4/2009 | Uthgenannt et al. |
| 2009/0125115 | A1 | 5/2009 | Popoola et al. |
| 2011/0015740 | A1* | 1/2011 | Metzger .................... A61F 2/38 |
| | | | 427/2.24 |
| 2011/0015750 | A1 | 1/2011 | Popoola et al. |
| 2011/0035018 | A1 | 2/2011 | Deffenbaugh et al. |
| 2011/0166664 | A1 | 7/2011 | Delfosse et al. |
| 2012/0209393 | A1 | 8/2012 | Ries et al. |
| 2012/0323335 | A1 | 12/2012 | Parisi et al. |
| 2013/0006354 | A1 | 1/2013 | Pressacco |
| 2013/0060344 | A1 | 3/2013 | Pierce |
| 2013/0110248 | A1 | 5/2013 | Zipnick |
| 2013/0131805 | A1 | 5/2013 | Hendriks et al. |
| 2015/0032218 | A1* | 1/2015 | Landon ................. A61F 2/3859 |
| | | | 623/20.35 |
| 2017/0225413 | A1 | 8/2017 | Larrouy et al. |
| 2018/0028718 | A1 | 2/2018 | Zhu et al. |
| 2018/0064543 | A1 | 3/2018 | Wright et al. |
| 2018/0296349 | A1* | 10/2018 | Stalcup .............. A61F 2/30771 |
| 2018/0325683 | A1 | 11/2018 | Logan et al. |
| 2019/0125541 | A1 | 5/2019 | Axelson et al. |
| 2019/0290441 | A1 | 9/2019 | Tong et al. |
| 2020/0179122 | A1* | 6/2020 | Stalcup ................. A61F 2/3877 |
| 2021/0059826 | A1 | 3/2021 | Gruczynski et al. |
| 2021/0177614 | A1 | 6/2021 | Webb et al. |
| 2021/0244545 | A1 | 8/2021 | Webb et al. |
| 2021/0361434 | A1* | 11/2021 | Zhang .................. A61F 2/3601 |

FOREIGN PATENT DOCUMENTS

| | | |
|---|---|---|
| EP | 2319462 B1 | 4/2013 |
| EP | 2740444 A1 | 6/2014 |
| EP | 2258319 B1 | 1/2016 |
| EP | 3257476 A1 | 12/2017 |
| EP | 3287101 A1 | 2/2018 |
| WO | 2016127281 A1 | 8/2016 |
| WO | 2016127282 A1 | 8/2016 |
| WO | 2016179728 A1 | 11/2016 |
| WO | 2017149279 A1 | 9/2017 |

* cited by examiner

METAL-REINFORCED POLYMER FEMORAL COMPONENT OF AN ORTHOPAEDIC KNEE PROSTHESIS AND ASSOCIATED METHOD OF MAKING THE SAME

TECHNICAL FIELD

The present disclosure relates generally to an implantable orthopaedic knee prosthesis, and more particularly to an implantable femoral component of an orthopaedic knee prosthesis.

BACKGROUND

During the lifetime of a patient, it may be necessary to perform a joint replacement procedure on the patient as a result of, for example, disease or trauma. As a result, joint arthroplasty has become a well-known surgical procedure by which the diseased and/or damaged natural joint is replaced by a prosthetic joint. For example, in a total knee arthroplasty surgical procedure, a patient's natural knee joint is partially or totally replaced by a prosthetic knee knee prosthesis. A typical knee prosthesis includes a tibial tray, a femoral component, and a polymer insert or bearing positioned between the tibial tray and the femoral component. In such a case, the femoral component is secured to a surgically-prepared distal end of the patient's femur, whereas the tibial tray is secured to a surgically-prepared proximal end of the patient's tibia. The polymer bearing is coupled to the tibial tray and thus provides a bearing surface upon which the femoral component articulates during extension and flexion of the knee.

A conventional femoral component is embodied as a monolithic metallic component constructed with an implant-grade biocompatible metal. Examples of such metals include cobalt, including cobalt alloys such as a cobalt chrome alloy, titanium, including titanium alloys such as a Ti6Al4V alloy, and stainless steel.

SUMMARY

According to an aspect of the disclosure, an orthopaedic knee prosthesis includes a femoral component. The femoral component includes a metal base that has an inferior base surface that is curved in the sagittal plane. The inferior base surface has a plurality of elongated ribs extending inferiorly therefrom. The metal base also has a superior base surface that includes a posterior fixation surface that extends generally in the superior/inferior direction, a distal fixation surface that extends generally in the anterior/posterior direction, a posterior-chamfer fixation surface that extends superiorly and posteriorly from the distal fixation surface in the direction toward the posterior fixation surface, an anterior fixation surface that extends generally in the superior/inferior direction, and an anterior-chamfer fixation surface that extends superiorly and anteriorly from the distal fixation surface in the direction toward the anterior fixation surface. The femoral component also includes a polymer articular layer molded to the inferior base surface of the metal base and into a plurality of elongated grooves defined by the plurality of ribs. The polymer articular layer has an articulation surface that is curved in the sagittal plane and configured to articulate with a bearing surface of a tibial component.

In an embodiment, a porous-metal coating is disposed on the superior base surface of the metal base.

The porous-metal coating may be disposed on the entirety of each of the posterior fixation surface, the distal fixation surface, the posterior-chamfer fixation surface, the anterior fixation surface, and the anterior-chamfer fixation surface of the superior base surface of the metal base.

In an embodiment, the metal base includes a number of lugs extending superiorly from the distal fixation surface, and the porous-metal coating is disposed on the lugs.

An inferior end of each of the plurality of ribs may have an undercut formed therein. The inferior ends of the plurality of ribs defining the undercuts may include rounded surfaces.

In an embodiment, the plurality of ribs extend in the sagittal plane. In another embodiment, the plurality of ribs extend in the coronal plane.

In an embodiment, the plurality of ribs are completely embedded in the polymer articular layer.

In an embodiment, a number of the plurality of ribs are hollow.

The polymer articular layer of the femoral component may be constructed with polyaryletherketone (PAEK). In other embodiments, the polymer articular layer of the femoral component is constructed with other biocompatible polymers, copolymers, and/or polymer blends.

In another aspect, an orthopaedic knee prosthesis system includes a tibial component configured to be implanted on a proximal end of a patient's tibia and a femoral component configured to be implanted on a distal end of a patient's femur. The tibial component includes a concave bearing surface. The femoral component includes a metal base that has an inferior base surface that is curved in the sagittal plane. A plurality of elongated ribs extend inferiorly from the inferior base surface. The metal base also includes a superior base surface having a number of bone fixation surfaces. A number of lugs extend superiorly from one of the number of bone fixation surfaces. The femoral component also includes a porous-metal coating disposed on the superior base surface of the metal base and the lugs. A polymer articular layer is molded to the inferior base surface of the metal base and into a plurality of elongated grooves defined by the plurality of ribs. The polymer articular layer has an articulation surface that is curved in the sagittal plane and configured to articulate with the bearing surface of the tibial component.

In an embodiment, the superior base surface includes a posterior fixation surface that extends generally in the superior/inferior direction, a distal fixation surface that extends generally in the anterior/posterior direction, a posterior-chamfer fixation surface that extends superiorly and posteriorly from the distal fixation surface in the direction toward the posterior fixation surface, an anterior fixation surface that extends generally in the superior/inferior direction, and an anterior-chamfer fixation surface that extends superiorly and anteriorly from the distal fixation surface in the direction toward the anterior fixation surface.

The porous-metal coating may be disposed on the entirety of each of the posterior fixation surface, the distal fixation surface, the posterior-chamfer fixation surface, the anterior fixation surface, and the anterior-chamfer fixation surface of the superior base surface of the metal base.

An inferior end of each of the plurality of ribs may have an undercut formed therein. The inferior ends of the plurality of ribs defining the undercuts may include rounded surfaces.

In an embodiment, the plurality of ribs extend in the sagittal plane. In another embodiment, the plurality of ribs extend in the coronal plane.

In an embodiment, the plurality of ribs are completely embedded in the polymer articular layer.

In an embodiment, a number of the plurality of ribs are hollow.

The polymer articular layer of the femoral component may be constructed with polyaryletherketone (PAEK). In other embodiments, the polymer articular layer of the femoral component is constructed with other biocompatible polymers, copolymers, and/or polymer blends.

According to another aspect, a method of making a femoral component of an orthopaedic knee prosthesis includes disposing a porous-metal coating onto a metal base. The metal base has a superior base surface that includes a number of bone fixation surfaces and a number of lugs. A polymer articular layer is molded onto an inferior base surface of the metal base that is curved in the sagittal plane such that a plurality of elongated ribs extending inferiorly from the inferior base surface are embedded in the polymer articular layer, and an outer surface of the polymer articular layer forms an articulation surface that is curved in the sagittal plane and configured to articulate with a bearing surface of a tibial component.

The porous-metal coating may be disposed onto the superior base surface and the number of lugs of the metal base by 3D-printing the porous-metal coating and the metal base as a monolithic metal component.

In an embodiment, an inferior end of each of the plurality of ribs has an undercut formed therein, and the polymer articular layer is molded onto the inferior base surface of the metal base such that polymer articular layer is molded to the undercuts of each of the plurality of ribs.

BRIEF DESCRIPTION

The detailed description particularly refers to the following figures, in which.

DETAILED DESCRIPTION

Figure 1:
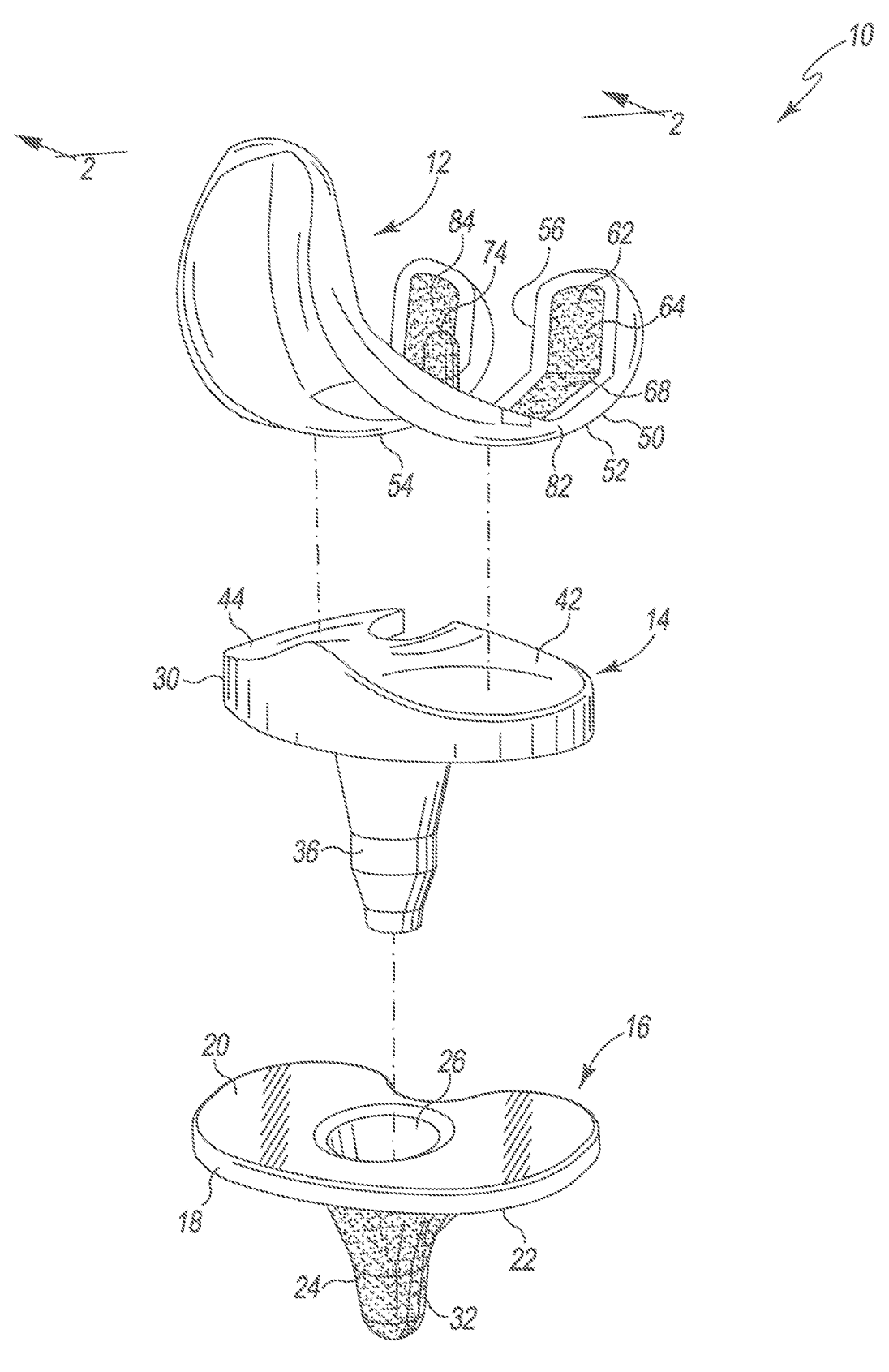
FIG. 1 is an exploded perspective view of an orthopaedic knee prosthesis that includes a metal-reinforced polymer femoral component, a tibial bearing, and a tibial tray.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
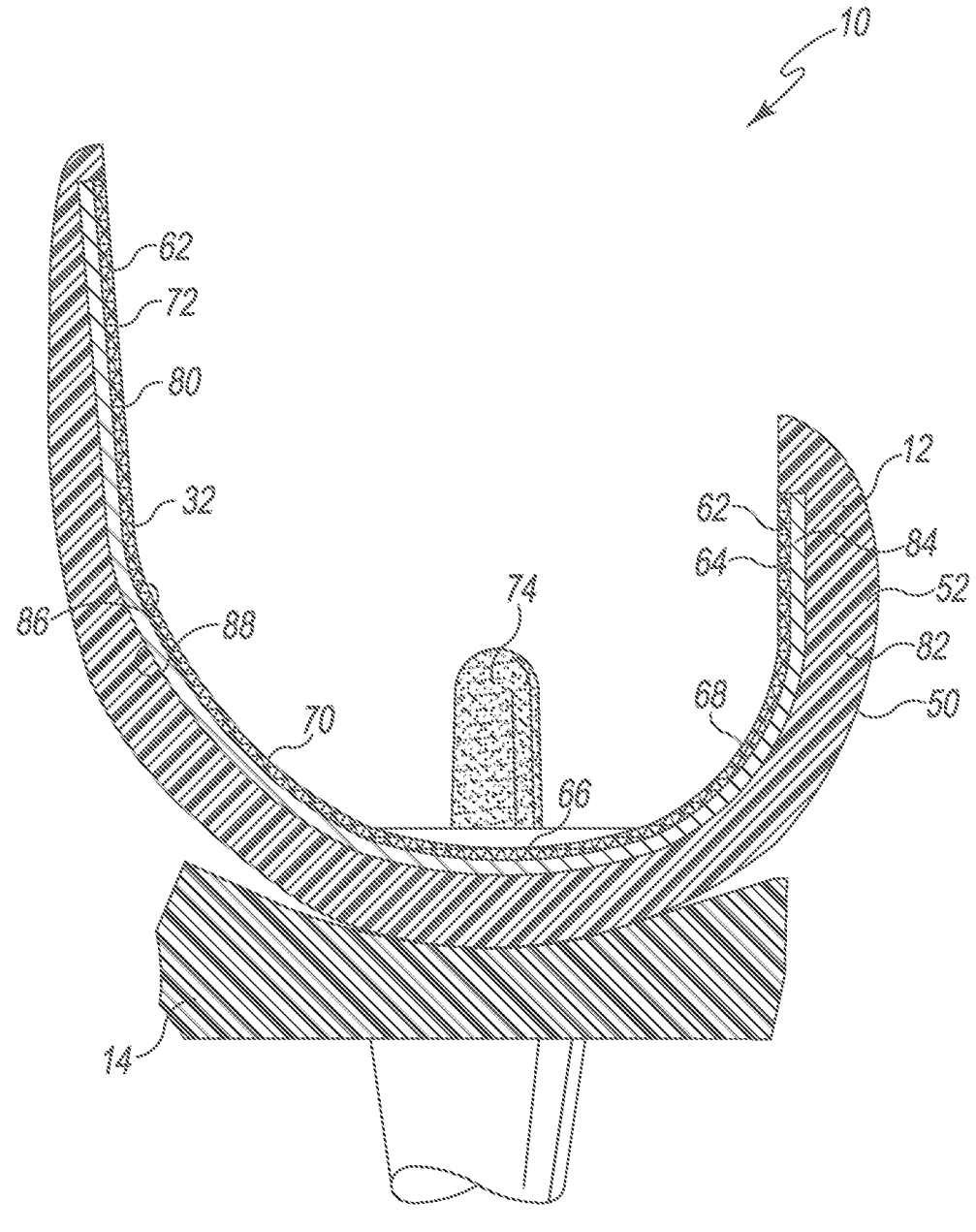
FIG. 2 is a cross-sectional view of the metal-reinforced polymer femoral component and the tibial bearing of FIG. 1 taken along the line 2-2 of FIG. 1, as viewed in the direction of the arrows.

Referring to FIGS. 1 and 2, there is shown an orthopaedic knee prosthesis 10 that includes a metal-reinforced polymer femoral component 12, a tibial bearing 14, and a tibial tray 16. The femoral component 12 is configured to articulate with the tibial bearing 14, which is configured to be coupled to the tibial tray 16. In the illustrative embodiment of FIG. 1, the tibial bearing 14 is embodied as a rotating or mobile tibial bearing and it is, therefore, rotatable relative to the tibial tray 16. However, in other embodiments, the tibial bearing 14 may be embodied as a fixed tibial bearing (not shown), which is restricted from rotating relative to the tibial tray 16.

The tibial tray 16 is configured to be secured to a surgically-prepared proximal end of a patient's tibia (not shown). The tibial tray 16 includes a platform 18 having a superior surface 20 and an opposite inferior surface 22. The tibial tray 16 also includes a stem 24 extending downwardly from the inferior surface 22 of the platform 18. A bore 26 is defined in the superior surface 20 of the platform 18 and extends inferiorly into the stem 24. The bore 26 is configured to receive a complimentary stem 36 of the tibial bearing 14 as discussed in more detail below.

The inferior surface 22 of the platform 18 and the stem 24 define a bone-engaging surface 28 of the tibial tray 16. As can be seen in FIG. 1, the bone-engaging surface 28 has a porous-metal coating 32 disposed thereon. It should be appreciated that the porous-metal coating 32 could be a separately-applied coating such as Porocoat®, Gription®, or Affixium® Porous Coatings which are commercially available from DePuy Synthes of Warsaw, Indiana. Alternatively, the porous-metal coating 32 is disposed on the metallic body 34 of the tibial tray 16 by virtue of being additively manufactured contemporaneously with the tray's metallic body 34 so as to create a common, monolithic component of the two metal structures.

As discussed above, the tibial bearing 14 is configured to be coupled with the tibial tray 16. The tibial bearing 14 includes a platform 30 having an upper bearing surface and a bottom bearing surface. In the illustrative embodiment in which the tibial bearing 14 is embodied as a rotating or mobile tibial bearing, the bearing 14 includes a stem 36 extending downwardly from the bottom surface of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments in which the tibial bearing 14 is embodied as a fixed tibial bearing, the bearing 14 may or may not include the stem 36 and/or may include other devices or features to secure the tibial bearing 14 to the tibial tray 16 in a non-rotating configuration. The upper bearing surface of the tibial bearing 14 includes a medial bearing surface 42 and a lateral bearing surface 44. The medial and lateral bearing surfaces 42, 44 are configured to receive or otherwise contact corresponding medial and lateral condyles 52, 54 of the femoral component 12. As such, each of the bearing surfaces 42, 44 has a concave contour.

Referring to FIG. 2, the femoral component 12 is configured to be coupled to a surgically-prepared surface of the distal end of a patient's femur (not shown). The femoral component 12 illustrated in FIGS. 1 and 2 is a posterior cruciate-retaining knee prosthesis and the tibial bearing 14 is embodied as a posterior cruciate-retaining tibial bearing 14. However, in other embodiments, the orthopaedic knee prosthesis 10 may be embodied as a posterior cruciate-sacrificing knee prosthesis (not shown).

As mentioned above, the femoral component 12 includes a pair of medial and lateral condyles 52, 54. The condyles 52, 54 are spaced apart to define an intracondylar notch 56 therebetween. In use, the condyles 52, 54 replace the natural condyles of the patient's femur. Each condyle 52, 54 of the femoral component 12 includes an outer articular surface 50, which is convexly curved in the sagittal plane and configured to articulate on the respective bearing surfaces 42, 44 of the tibial bearing 14.

Opposite to the articular surface 50, the femoral component 12 includes a bone-engaging surface 62. The bone-engaging surface 62 contacts the surgically-prepared distal femur of the patient. The bone-engaging surface 62 includes multiple surfaces that mate with planar surfaces surgically cut into the patient's distal femur. For example, as shown in FIG. 2, a pair of posterior fixation surfaces 64 are opposite the posterior surfaces of the condyles 52, 54, with one of the posterior fixation surfaces 64 being the medial fixation surface, the other the lateral fixation surface. As can be seen in FIGS. 1 and 2, the posterior fixation surfaces 64 extend generally in the superior/inferior direction. A pair of distal fixation surfaces 66 (one being medially positioned, the other the laterally positioned) is opposite the distal surfaces of the condyles 52, 54 and extend generally in the anterior/posterior direction. A pair of posterior-chamfer fixation surfaces 68 (one being medially positioned, the other the laterally positioned) is opposite the posterior-chamfer surfaces of the condyles 52, 54. The medial and lateral posterior-chamfer fixation surfaces 68 extend superiorly and posteriorly from their respective medial and lateral distal fixation surfaces 66 in the direction toward their respective posterior fixation surfaces 64. The medial and lateral anterior-chamfer fixation surfaces 70 are opposite the anterior-chamfer surfaces of the condyles 52, 54, respectively, and extend superiorly and anteriorly away from their respective distal fixation surfaces 66 in the direction toward an anterior fixation surface 72. The anterior fixation surface 72 is opposite the anterior condyle surface and, like the posterior fixation surfaces 64, extends generally in the superior/inferior direction.

The bone-engaging surface 62 of the femoral component 12 may also include the outer surfaces of a pair of lugs 74 extending superiorly from the distal fixation surfaces 66. The lugs 74 are configured to be received into holes formed in the surgically-prepared distal femur of the patient during installation of the femoral component 12.

The femoral component 12 described herein is embodied as a metal-reinforced polymer component. As such, the femoral component 12 includes a polymer articular layer 82 molded onto a metal base 84 so as to create a one-piece (i.e., non-modular) final product. The articular surface 50 of the femoral component 12 is formed in the polymer articular layer 82 of the femoral component 12 thus defining a polymeric articular surface that is configured to articulate on the bearing surfaces 42, 44 of the tibial bearing 14.

The polymer articular layer 82 of the femoral component 12 is embodied as a monolithic polymer body constructed with a material that allows for smooth articulation between the femoral component 12 and the tibial bearing 14 (which is generally constructed with a biocompatible polymer such as polyethylene, including ultrahigh molecular weight polyethylene (UHMWPE)). A polymer or a blend of polymers is preferably used to construct the polymer articular layer 82. As used herein, the term "polymer" is intended to mean any polymeric material which may be implanted into a patient. Specific examples of polymers that may be used in the construction of the femoral component 12 are the polyaryletherketone (PAEK) family, the polysulfone family, the polyimide family, and the polyacetal family. The term "polyaryletherketone," as defined herein, includes polyetheretherketone (PEEK), polyetherketone, and polyetherketoneetherketoneketone or any other type of polyaryletherketone used in the construction of a prosthetic implant, including PEEK blends such as PEEK-polyetherimide and PEEK-polyphenylsulfone blends.

It should be appreciated that, as used herein, the term "layer" is not intended to be limited to a "thickness" of material positioned proximate to another similarly dimensioned "thickness" of material, but rather is intended to include numerous structures, configurations, and constructions of material. For example, the term "layer" may include a portion, region, or other structure of material which is positioned proximate to another portion, region, or structure of differing material.

Figures 3, 4:
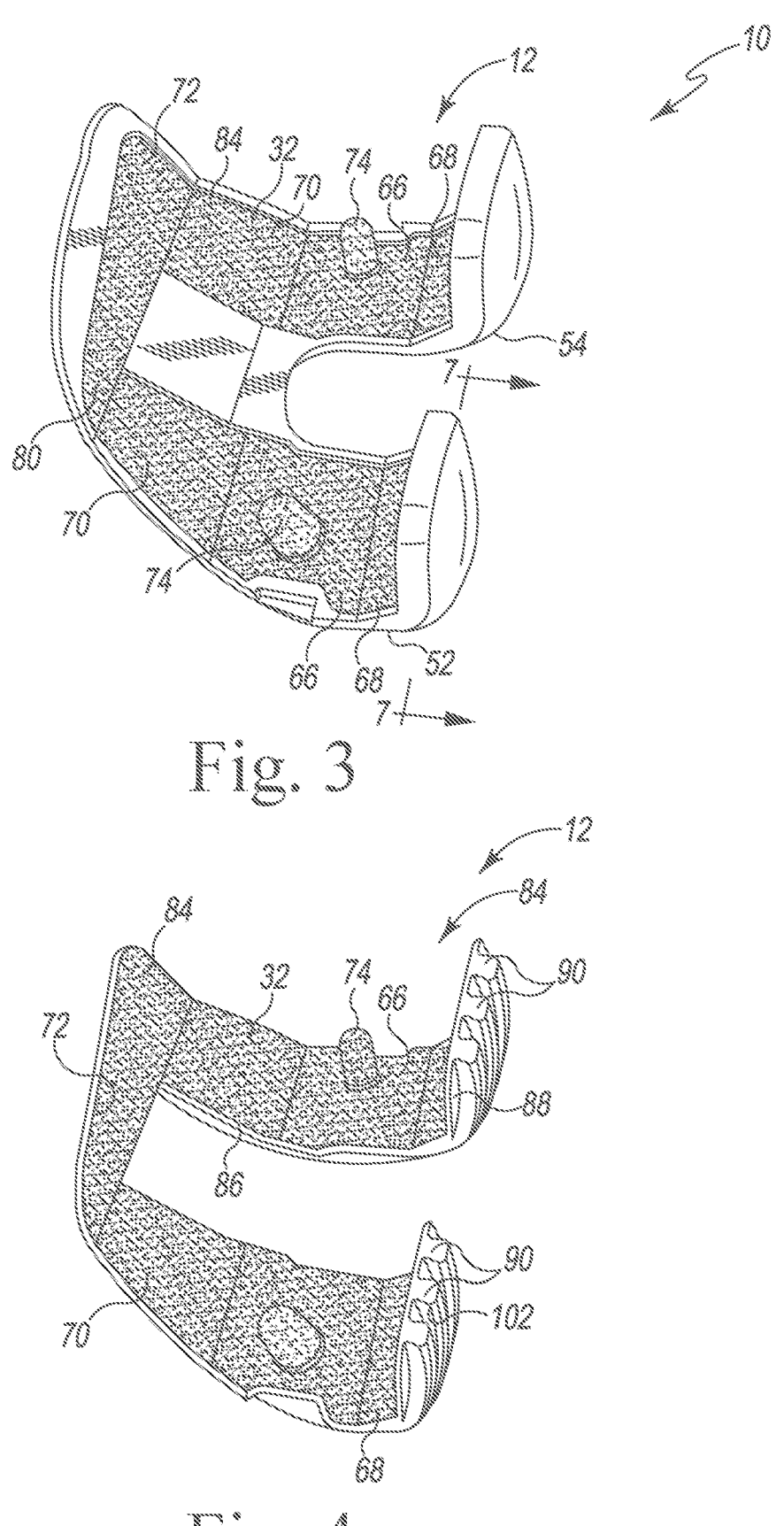
FIG. 3 is a perspective view of the metal-reinforced polymer femoral component of the orthopaedic knee prosthesis of FIG. 1.
FIGS. 4 and 5 are perspective views of the metal base of the metal-reinforced polymer femoral component of FIG. 3.
Figures 5, 6:
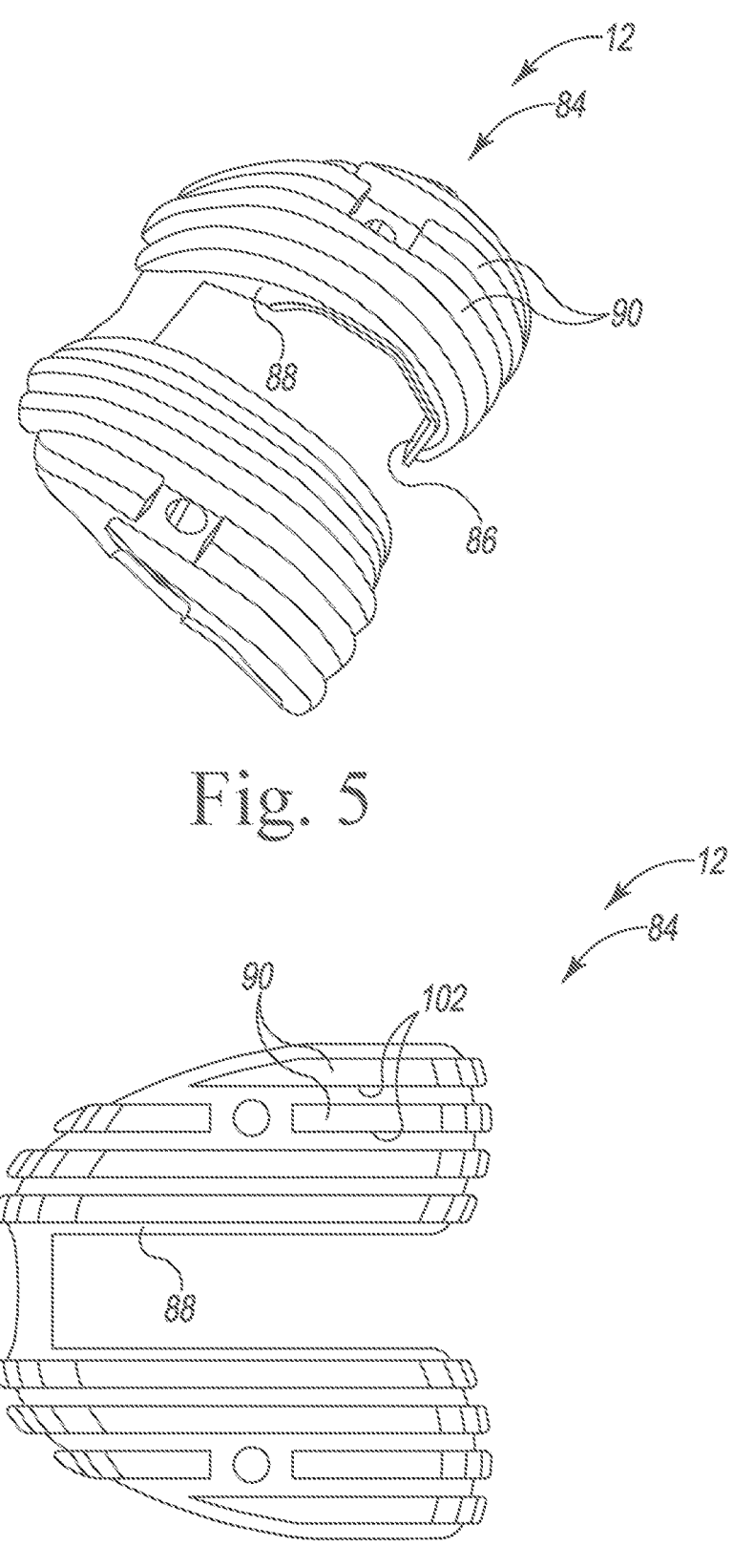
FIG. 6 is an inferior side elevation view of the metal base of FIGS. 4 and 5.

Referring now to FIGS. 4-7, the metal base 84 is shown in more detail. As can be seen best in FIG. 4 (and in the cross section of FIG. 2), the metal base 84 of the femoral component 12 includes a superior base surface 86 that includes the component's bone-engaging surface 62 and an opposite inferior base surface 88 onto which the polymer articular layer 82 is molded. As can be seen in FIGS. 2-4, the posterior fixation surfaces 64, the distal fixation surfaces 66, the posterior-chamfer fixation surfaces 68, the anterior-chamfer fixation surfaces 70, and the anterior fixation surface 72 are formed in the superior base surface 86.

Figure 7:
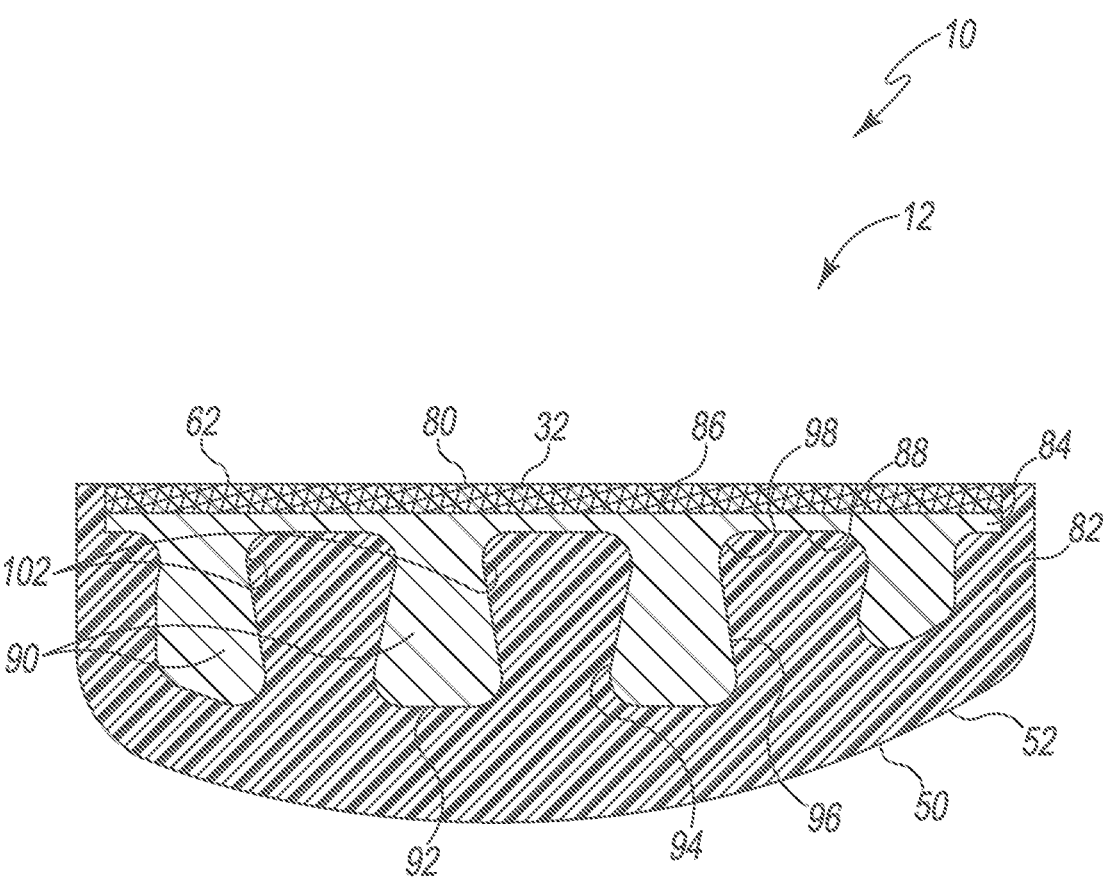
FIG. 7 is an enlarged cross-sectional view taken along the line 7-7 of FIG. 3, as viewed in the direction of the arrows, note the porous-metal coating is not shown in cross section in FIG. 7 for clarity of description.

As can be seen in FIGS. 2 and 4, the inferior base surface 88 is curved in the sagittal plane and extends generally parallel to the femoral component's articular surface 50. A plurality of elongated ribs 90 extend inferiorly from the inferior base surface 88. Like the inferior base surface 88, the elongated ribs 90 extend in the sagittal plane. An inferior end 92 of each of the plurality of ribs 90 has an undercut 94 formed therein. Specifically, the inferior ends 92 of each of the ribs 90 is wider than the opposite ends of the ribs 90 (i.e., the ends of the ribs 90 that are secured to the inferior base surface 88). As can be seen in FIG. 7, the ribs 90 extend from their inferior ends 92 along a convex surface 96 that transitions to a concave surface 98 prior transitioning to the inferior base surface 88 thereby creating the undercuts 94. It should be appreciated that although the undercuts 94 are shown as blended-radius undercuts 40 (i.e., the surfaces defining the undercuts are rounded), other configurations are also contemplated including, for example, undercuts that that are more squared off in design (e.g., the ribs 90 define orthogonal transitions instead of rounded transitions).

As can be seen in FIG. 7, the surfaces of the ribs 90 defining the undercuts 94 create a combined surface that faces away from the inferior base surface 88 of the metal base 84 to which the polymer articular layer 82 is molded. In such a way, the undercuts 94 resist pull-off of the polymer articular layer 82 from the metal base 84.

It should be appreciated that although the ribs 90 are herein described as extending in the sagittal plane, other configurations of the ribs 90 may also be used to fit the needs of a given design of the femoral component 12. For example, the ribs 90 may be arranged to extend in the coronal plane.

As a further example, the ribs 90 may be arranged to extend in both the sagittal and the coronal plane.

It should also be appreciated that the number and geometry (e.g., length, width, cross-sectional shape, etc.) of the ribs 90 may be altered to fit the needs of a given design of the femoral component 12 and/or to impart desired properties into a given design of the femoral component 12. For example, the stiffness of the metal base 84 may be controlled as a function of the number of ribs 90 and the cross-sectional shape of the ribs 90. Furthermore, the ribs 90 may be configured as hollow structures (by the use of 3D printing, for example). Doing so creates an outer rib geometry that is useful in molding the polymer articular layer 82 to the metal base 84, while also allowing the overall stiffness of the femoral component 12 to be controlled by altering the wall thickness of the hollow ribs. In such an embodiment, the wall thickness could be uniform throughout the cross section of the ribs 90 or thicker in some regions (e.g., the inferior ends 92 of the ribs 90) and thinner in other areas based on the structural stiffness desired in a given design of the femoral component 12.

The femoral component 12 is embodied as a cementless component—that is, the femoral component 12 is designed to be installed on the surgically-prepared distal end of a patient's femur without the use of bone cement. As such, the bone-engaging surface 62 of the femoral component has the porous-metal coating 32 disposed thereon. Similarly to the tibial tray 16, the porous-metal coating 32 disposed on the femoral component 12 may be a separately-applied coating (e.g., Porocoat®, Gription®, or Affixium® Porous Coatings). However, in the illustrative embodiment described herein, the porous-metal coating 32 is disposed on the metal base 84 by virtue of being additively manufactured contemporaneously with the metal base 84 so as to create a common, monolithic component of the two metal structures. For example, Affixium® Porous Coating may be additively manufactured contemporaneously with the metal base so as to create a common, monolithic component.

In one example, the porous-metal coating 32 may be made of a porous material 80 as described in U.S. patent application Ser. No. 16/365,557, which was filed Mar. 26, 2019 and is assigned to the same assignee as the present disclosure, the disclosure of which is hereby incorporated by reference as if set forth in its entirety herein. Additive manufacturing processes can include, by way of example, powder bed fusion printing, such as melting and sintering, cold spray 3D printing, wire feed 3D printing, fused deposition 3D printing, extrusion 3D printing, liquid metal 3D printing, stereolithography 3D printing, binder jetting 3D printing, material jetting 3D printing, and the like.

In one example, referring to FIG. 7, the porous material 80 of the porous-metal coating 32 can be defined by a porous three-dimensional structure that can includes a plurality of connected unit cells. Each unit cell can define a unit cell structure that includes a plurality of lattice struts that define an outer geometric structure and a plurality of internal struts that define a plurality of internal geometric structures that are disposed within the outer geometric structure. In one example, the outer geometric structure may be a rhombic dodecahedron, and the inner geometric structures may be a rhombic trigonal trapezohedron. It should be appreciated that such geometric structures may vary to fit the needs of a given design. Further, it should be appreciated that the unit cells that make up the porous-metal coating 32 may also have any suitable alternative geometry to fit the needs of a given design.

The porous material 80 is formed from a metal powder. Illustratively, the metal powders may include, but are not limited to, titanium, titanium alloys, stainless steel, cobalt chrome alloys, tantalum, or niobium powders. The porous-metal coating 32 has a porosity suitable to facilitate bony ingrowth into the femoral component 12 when the superior base surface 86 and the lugs 74 of the metal base 84 are implanted into the surgically-prepared posterior surface of the patient's patella.

In the illustrative embodiment described herein, the porous-metal coating 32 is additively manufactured directly onto the superior base surface 86 and the lugs 74 of the metal base 84. In such an embodiment, the two structures—i.e., the metal base 84 and the porous-metal coating 32—may be manufactured contemporaneously during a common additive manufacturing process. For example, the two structures may be manufactured contemporaneously in a single 3D printing operation that yields a common, monolithic metallic component including both structures. Alternatively, the porous-metal coating 32 could be manufactured as a separate component that is secured to the metal base 84.

The polymer articular layer 82 may be assembled to the metal base 84 by use of a number of different techniques. One exemplary manner for doing so is by use of compression molding techniques. For example, the metal base 84 and the material from which the polymer articular layer 82 is to be made (e.g., PEEK) may be placed in a mold with one another. Thereafter, the components are compression molded to one another under process parameters which cause the material from which the polymer articular layer 82 is made (e.g., PEEK) to be molten and mechanically secured to the metal base 84 by the compression molding process. As described above, the molten polymer articular layer 82 interdigitates with the ribs 90 of the metal base 84 when molded thereto (i.e., the molten polymer articular layer 82 is injected into the grooves 102 defined by the ribs 90). It should also be appreciated that the mold may be configured to not only mold the components to one another, but also form the articular surface 50 of the femoral component 12 into the polymer articular layer 82. Another illustrative, and equally effective, method of assembling the polymer articular layer 82 to the metal base 84 is by the use of injection molding.

The starting materials (e.g., polymers such as PEEK) for use in the molding process may be provided in a number of different forms. For example, each of the starting materials may be provided as a preform. What is meant herein by the term "preform" is an article that has been consolidated, such as by ram extrusion or compression molding of polymer resin particles, into rods, sheets, blocks, slabs, or the like. The term "preform" also includes a preform "puck" which may be prepared by intermediate machining of a commercially available preform. Polymer preforms may be provided in a number of different pre-treated or preconditioned variations. For example, crosslinked or non-crosslinked (e.g., irradiated or non-irradiated) preforms may be utilized. Such preforms may be treated to eliminate (e.g., re-melting or quenching) or stabilize (e.g., the addition of vitamin E as an antioxidant) any free radicals present therein. Alternatively, the preforms may not be treated in such a manner.

The starting materials (e.g., polymers, copolymers, and/or blended polymers) may also be provided as powders or pellets. What is meant herein by the terms "powder" and "pellets" are resin particles. Similarly to as described above in regard to preforms, powders and/or pellets may be provided in a number of different pre-treated or preconditioned variations. For example, crosslinked or non-crosslinked (e.g., irradiated or non-irradiated) powders and/or pellets may be utilized. Moreover, in the case of blended polymers, the powder and/or pellets may be provided as pre-blended resin particles or blended in situ in a hopper associated with the molding machine to produce the desired blend composition for use in the molding process.

As described herein, the metal-reinforced femoral component 12 has certain enhanced properties. For example, use of the ribbed metal base 84 increases the overall stiffness of the component and creates a uniform wall thickness for accurate injection molding of the polymer articular layer 82.

In some designs of the femoral component 12, an alternative to use of the metal base 84 includes sprayed coatings. For example, a titanium plasma spray (TPS) coating may be applied to a previously-molded polymer femoral component to provide a metal layer on the backside of the component. Another alternative approach is the use of a two-shot molding process. In such a case, the polymer articular layer 82 is formed in a first shot with a porous coating then being applied to the backside of the articular layer 82 via a porogen-filled second shot.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic knee prosthesis, comprising:
a femoral component, comprising:
a metal base comprising (i) an inferior base surface that is curved in the sagittal plane, the inferior base surface having a plurality of elongated ribs extending inferiorly therefrom, and (ii) a superior base surface having a porous-metal coating disposed thereon, the superior base surface comprising (a) a posterior fixation surface that extends generally in the superior/inferior direction, (b) a distal fixation surface that extends generally in the anterior/posterior direction, (c) a posterior-chamfer fixation surface that extends superiorly and posteriorly from the distal fixation surface in the direction toward the posterior fixation surface, (d) an anterior fixation surface that extends generally in the superior/inferior direction, and (e) an anterior-chamfer fixation surface that extends superiorly and anteriorly from the distal fixation surface in the direction toward the anterior fixation surface, and
a polymer articular layer molded to the inferior base surface of the metal base and into a plurality of elongated grooves defined by the plurality of ribs, the polymer articular layer having an articulation surface that is curved in the sagittal plane and configured to articulate with a bearing surface of a tibial component.

2. The orthopaedic knee prosthesis of claim 1, wherein a porous-metal coating is disposed on the entirety of each of the posterior fixation surface, the distal fixation surface, the posterior-chamfer fixation surface, the anterior fixation surface, and the anterior-chamfer fixation surface of the superior base surface of the metal base.

3. The orthopaedic knee prosthesis of claim 1, wherein:
the metal base includes a number of lugs extending superiorly from the distal fixation surface, and
a porous-metal coating is disposed on the superior base surface of the metal base and the lugs.

4. The orthopaedic knee prosthesis of claim 1, wherein an inferior end of each of the plurality of ribs has an undercut formed therein.

5. The orthopaedic knee prosthesis of claim 4, wherein the inferior ends of the plurality of ribs defining the undercuts comprise rounded surfaces.

6. The orthopaedic knee prosthesis of claim 1, wherein the plurality of ribs extend in the sagittal plane.

7. The orthopaedic knee prosthesis of claim 1, wherein the plurality of ribs extend in the coronal plane.

8. The orthopaedic knee prosthesis of claim 1, wherein the plurality of ribs are completely embedded in the polymer articular layer.

9. The orthopaedic knee prosthesis of claim 1, wherein a number of the plurality of ribs are hollow.

10. The orthopaedic knee prosthesis of claim 1, wherein the polymer articular layer of the femoral component comprises polyaryletherketone (PAEK).

11. An orthopaedic knee prosthesis system, comprising:
a tibial component configured to be implanted on a proximal end of a patient's tibia, the tibial component including a concave bearing surface, and
a femoral component configured to be implanted on a distal end of a patient's femur, the femoral component comprising:
a metal base comprising (i) an inferior base surface that is curved in the sagittal plane, the inferior base surface having a plurality of elongated ribs extending inferiorly therefrom, and (ii) a superior base surface having (a) a number of bone fixation surfaces, and (b) a number of lugs extending superiorly from one of the number of bone fixation surfaces,
a porous-metal coating disposed on the superior base surface of the metal base and the lugs, and
a polymer articular layer molded to the inferior base surface of the metal base and into a plurality of elongated grooves defined by the plurality of ribs, the polymer articular layer having an articulation surface that is curved in the sagittal plane and configured to articulate with the bearing surface of the tibial component.

12. The orthopaedic knee prosthesis system of claim 11, wherein the number of bone fixation surfaces of the superior base surface comprises:
a posterior fixation surface that extends generally in the superior/inferior direction,
a distal fixation surface that extends generally in the anterior/posterior direction,
a posterior-chamfer fixation surface that extends superiorly and posteriorly from the distal fixation surface in the direction toward the posterior fixation surface,
an anterior fixation surface that extends generally in the superior/inferior direction, and an anterior-chamfer fixation surface that extends superi-
orly and anteriorly from the distal fixation surface in
the direction toward the anterior fixation surface.

13. The orthopaedic knee prosthesis system of claim 12,
wherein the porous-metal coating is disposed on the entirety
of each of the posterior fixation surface, the distal fixation
surface, the posterior-chamfer fixation surface, the anterior
fixation surface, and the anterior-chamfer fixation surface of
the superior base surface of the metal base.

14. The orthopaedic knee prosthesis system of claim 11,
wherein an inferior end of each of the plurality of ribs has
an undercut formed therein.

15. The orthopaedic knee prosthesis system of claim 14,
wherein the inferior ends of the plurality of ribs defining the
undercuts comprise rounded surfaces.

16. The orthopaedic knee prosthesis system of claim 11,
wherein the plurality of ribs extend in the sagittal plane.

17. The orthopaedic knee prosthesis system of claim 11,
wherein the plurality of ribs extend in the coronal plane.

18. The orthopaedic knee prosthesis system of claim 11,
wherein the plurality of ribs are completely embedded in the
polymer articular layer.

19. The orthopaedic knee prosthesis of claim 11, wherein
a number of the plurality of ribs are hollow.

20. The orthopaedic knee prosthesis system of claim 11,
wherein the polymer articular layer of the femoral compo-
nent comprises polyaryletherketone (PAEK).

\*    \*    \*    \*    \*